United States Patent [19]

Veloso et al.

[11] Patent Number: 5,444,156
[45] Date of Patent: Aug. 22, 1995

[54] MONOCLONAL ANTIBODIES TO HUMAN PLASMA PREKALLIKREIN

[75] Inventors: Dulce C. Veloso, Philadelphia; Robert W. Colman, Moylan, both of Pa.

[73] Assignee: Temple University-of The Commonwealth System of Higher Education, Philadelphia, Pa.

[21] Appl. No.: 19,953

[22] Filed: Feb. 19, 1993

Related U.S. Application Data

[63] Continuation of Ser. No. 179,706, Apr. 11, 1988, abandoned, which is a continuation-in-part of Ser. No. 883,218, Jul. 8, 1986, abandoned, which is a continuation-in-part of Ser. No. 754,800, Jul. 12, 1985, abandoned.

[51] Int. Cl.⁶ ............................................. C07K 16/40
[52] U.S. Cl. ............................ 435/240.27; 435/70.21; 530/388.25
[58] Field of Search ................. 530/388.25; 430/70.21, 430/172.2, 240.26

[56] References Cited

FOREIGN PATENT DOCUMENTS 080279 6/1983 European Pat. Off. .
085402 8/1983 European Pat. Off. .
100395 2/1984 European Pat. Off. .

OTHER PUBLICATIONS

Donaldson et al., 1977, J. Clin. Invest., 60:571–583, Prekallikrein . . . , Defect.
Goding et al, 1983, Monoclonal . . . Practice, pp. 57–97.
Scott et al, 1979, Eur. J. Biochem., 100:77.
DeAgostini et al., *Kinin '84 Savannah International Congress,* Oct. 21–25, 1984, Abstracts p. 11.
Bagdasarian et al., *J. Clin. Invest.* 54:1444–54 (1974).
Veloso et al., *Thromb. Haemostas.* 54 (1): 252 (Jul. 14, 1985).
Veloso et al., *Thromb. Haemostas* 58 (1): 28 (Jul. 6, 1987).
Veloso et al., *Kinin '87 Tokyo International Congress* Nov. 29–Dec. 3, 1987, Tokyo, Japan; Abstracts, p. 94.
Veloso et al., *Fed. Proc.* 45 (6): 1638 (May, 1986).
Veloso et al., *Fed. Proc.* 46 (6): 2024 (May 1, 1987).
Veloso et al., *Blood* 70 (4):1053–1062 (Oct. 1987).
DeAgostini et al., *Thromb. Haemostas* 54 (1):228 (Jul. 1985).
DeAgostini et al., *Proc. Natl. Acad. Sci.* USA 82:5910–5913 (Aug. 1985).
Lewin et al., *J. Biol. Chem.* 258: 6415–6421 (1983).
Colman et al., *J. Clin. Invest.* 61: 287–296 (1978).
Bedi et al., Hybridoma 3(3), 287–92 (Oct. 31, 1984).
Patent Abstracts of Japan, vol. 7, No. 274 (P241) [1419](Dec. 7, 1983) Abstracting Jap. Pat. Apln. 58–151560 (1983).
Patent Abstracts of Japan, vol. 10, No. 305 (P–507) [2361] (Oct. 17, 1986) Abstracting Jap. Pat. Apln. 61–118663 (1986).

*Primary Examiner*—David L. Lacey
*Assistant Examiner*—F. Christopher Eisenchenk
*Attorney, Agent, or Firm*—Seidel Gonda Lavorgna & Monaco

[57] ABSTRACT

Four novel cell lines, ATCC #HB-8862 through ATCC #HB-8865 produce monoclonal antibody to human plasma prekallikrein. At least three of the antibodies also recognize plasma kallikrein, specifically the heavy chain thereof, and kallikrein-Cl-inhibitor complex; at least one of these three antibodies recognizes kallikrein-alpha$_2$-macroglobulin complex and kallikrein-antithrombin III complex. The antibodies do not cross-react with tissue kallikrein. The hybridomas are formed by fusing spleen cells from immunized BALB/c AnSkh mice with SP2/O-Agl4 myeloma cells. Diagnostic and biochemical uses of the monoclonal antibodies are provided.

24 Claims, 3 Drawing Sheets

MONOCLONAL ANTIBODIES TO HUMAN PLASMA PREKALLIKREIN

REFERENCE TO GOVERNMENT GRANT

The invention described herein was supported in part by National Institutes of Health grant HL24365. The Government has certain rights in the invention.

CROSS-REFERENCE TO RELATED APPLICATIONS

This application is a continuation of application Ser. No. 07/179,706, filed Apr. 11, 1988, now abandoned, which is a continuation-in-part of application Ser. No. 06/883,218, filed Jul. 8, 1986, now abandoned, which is a continuation-in-part of application Ser. No. 06/754,800, filed Jul. 12, 1985, now abandoned.

FIELD OF THE INVENTION

This invention relates to hybrid cell lines for production of monoclonal antibodies to human plasma prekallikrein, a protein which is found in nearly all human blood. The invention also relates to the antibody produced by these cell lines, and to diagnostic, therapeutic and biochemical methods and compositions using the same.

BACKGROUND OF THE INVENTION

Prekallikrein is a single-chain glycoprotein which is present in human blood in at least two forms having molecular weights of 85 kDa and 88 kDa, respectively. Prekallikrein is one of five plasma proteins which are junction-initiating and/or modulatory proteins for coagulation, fibrinolysis, complement activation, prorenin activation, and possibly other biochemical pathways occurring in the plasma. Colman, R. W., J. Clin, Inv. 73:1249–1253 (1984). The other major junction-initiating or modulatory plasma proteins are (1) factor XII, also known as Hageman factor, (2) high molecular weight kininogen, (3) Cl-inhibitor and (4) alpha$_2$-macroglobulin.

Prekallikrein and factor XII are plasma serine protease zymogens. Conversion of prekallikrein to the active enzyme kallikrein is initiated by factor XII autoactivated to factor XIIa in the presence of negatively charged surfaces. Factor XIIa or an activated fragment of factor XII (factor XIIf) cleaves prekallikrein into kallikrein. Kallikrein activates factor XII to produce additional factor XIIa. Kallikrein consists of two polypeptides linked together by one or more disulfide bridges. One of the kallikrein polypeptides, known as the "heavy chain", has a molecular weight of 53 kDa. The other polypeptide, known as the "light chain" has two variants, 33 kDa and 37 kDa, respectively, depending on the form of prekallikrein from which they originate. The light chain contains the enzyme active site. The 33 kDa kallikrein light chain originates from the 85 kDa prekallikrein, while the 37 kDa variant is from the 88 kDa form of prekallikrein.

Prekallikrein is present in blood as a non-covalent complex with high molecular weight kininogen. The latter is a cofactor for both factor XIIa and kallikrein. It is also a substrate of kallikrein. Kallikrein cleaves high molecular weight kininogen into four fragments: three polypeptides and the potent vasodepressor peptide bradykinin. Other substrates of kallikrein include plasminogen and prorenin. In addition, kallikrein stimulates neutrophil aggregation and degranulation.

Cl-inhibitor and alpha$_2$-macroglobulin are the two major plasma protease inhibitors. Other inhibitors such as antithrombin III can contribute about 13% to kallikrein inhibition of surface-activated normal plasma in vitro. Inhibition by these minor inhibitors may be higher in situations where Cl-inhibitor and alpha$_2$-macroglobulin are depleted or inactivated.

Cl-inhibitor inhibits kallikrein by forming a covalent complex with it. Alpha$_2$-macroglobulin inhibits kallikrein by combining with kallikrein to form a partially inactive complex. Cl-inhibitor and alpha$_2$-macroglobulin thus regulate the activity of kallikrein in the body. Kallikrein is also inhibited by combining with antithrombin III.

A deficiency of Cl-inhibitor gives rise to the classic disease hereditary angioedema and a decrease in the level of functional prekallikrein without change in prekallikrein/kallikrein antigen. Activation of prekallikrein may be inferred from a drop in its plasma level, by formation of kallikrein-Cl-inhibitor complex, or by the release of bradykinin into the circulation, concomitant with cleavage of plasma high molecular weight kininogen. The appearance of these signals has been demonstrated in a variety of diseases, most notably gram negative septicemia. Colman, R. W., J. Clin. Inv. 73:1249–1253 (1984). This affliction is a major cause of death and disability among hospitalized patients, with an incidence of several hundred thousand cases each year. Hypotension and hemorrhage are frequent complications due to activation of the contact phase of blood coagulation. Endotoxin infusion leads to activation of factor XII, which in turn cleaves prekallikrein to the active form kallikrein, resulting in a drop in the level of prekallikrein in the plasma. When kallikrein inhibitors are consumed, the concentration of the active form, kallikrein (as distinguished from the inactive form, prekallikrein), is increased. Early detection of this change in plasma prekallikrein and kallikrein levels allows intervention with treatment before the occurrence of irreversible shock.

Kohler and Milstein, Nature 256, 493–497 (1975) were the first to describe the fusion of myeloma cells to immune spleen cells from mice to generate continuous cell lines. These hybrid cell lines, or hybridomas, have characteristics that neither the parental myeloma cells nor parental immune spleen cells possess. Hybridomas are capable of continuously producing homogeneous (monoclonal) antibodies which recognize a single antigenic determinant. Prior to the work of Kohler and Milstein, only polyclonal antisera could be obtained, which are not capable of continuously producing identical antibodies. Polyclonal antibodies recognize a number of different antigenic determinants. Because of homology among the polypeptides containing the active site of several serine proteases, and homology between the heavy chains of prekallikrein and factor XI, thorough characterization of antibodies is necessary for diagnostic utility, which could be difficult and time-consuming in the case of polyclonal antibodies.

Although techniques for the production of hybridomas are now extensively described in the literature, e.g., *Monoclonal Antibodies, Hybridomas: A New Dimension In Biological Analysis*, R. H. Kennett, T. J. McKearn, and K. B. Bechtol, eds., Plenum Press, New York and London (1980), there is no general method for obtaining successful monoclonal antibody-producing hybridomas which can be used with all antigens. Fusion techniques must be varied in each case to obtain hybridomas producing monoclonal antibody to the desired antigen. In order to obtain antibodies specific to a single antigen, laborious purification techniques are required to provide highly purified antigen for either immunization or screening. The production of monoclonal antibodies for any given antigen is still a highly empirical process.

There have been no previous reports of monoclonal antibodies against human plasma prekallikrein, although plasma prekallikrein is present in all humans with very few exceptions. Prekallikrein and kallikrein are detected in patient blood by means of coagulant and immunochemical assays using polyclonal antisera. The dearth of literature accounts of monoclonal antibodies to prekallikrein is no doubt due to difficulties in the purification of antigen and/or the lack of success in preparation of suitable hybridomas.

SUMMARY OF THE INVENTION

According to the present invention, novel hybridomas have been prepared providing cell lines producing monoclonal antibodies which specifically bind to an antigenic determinant of human plasma prekallikrein. Each hybridoma comprises a cell hybrid formed by fusion of cells from a myeloma line and spleen cells from a donor previously immunized with human plasma prekallikrein. The hybridomas are, respectively, ATCC #HB-8862 through #HB-8865. Each antibody so produced is specific for an antigenic determinant of human plasma prekallikrein. For at least #HB-8862, -8863 and -8864, the antigenic determinant of prekallikrein so recognized is also shared by plasma kallikrein and kallikrein-Cl-inhibitor complex. For at least #HB-8862, the antigenic determinant so recognized is further shared by kallikrein-alpha$_2$-macroglobulin complex and kallikrein-antithrombin III complex. The antigenic determinant is contained in the kallikrein heavy chain. The purified monoclonal antibody contains essentially no other anti-human immunoglobulin. The hybridomas may be cultured in vitro to produce antibodies.

The hybrid cell lines of the present invention may be prepared by first immunizing mice with purified human plasma prekallikrein. The spleen cells are then removed and a suspension thereof is made. The spleen cells are fused with mouse myeloma cells in the presence of a fusion promotor. The fused cells are diluted and cultured in separate wells in a medium which will not support the unfused myeloma cells. The supernatant in each well is assayed for the presence of antibody to human plasma prekallikrein by enzyme-linked immunosorbent assay ("ELISA"). Hybridomas secreting antibody which binds to human plasma prekallikrein are selected and cloned.

The hybridomas are cultured in a suitable medium and the antibody is recovered from the supernatant. Alternatively, the clones are transferred intraperitoneally into mice, and the resulting malignant ascites and serum containing the desired antibody are harvested.

Methods for detecting the level of human plasma prekallikrein in specimens of interest are provided. The specimen is incubated with an excess of a kallikrein inhibitor selected from the group consisting of Cl-inhibitor, alpha$_2$-macroglobulin and antithrombin III, to convert all kallikrein to kallikrein-inhibitor complex. By "excess" is meant sufficient kallikrein inhibitor to convert all kallikrein in the specimen to kallikrein-inhibitor complex. The kallikrein-inhibitor complexes are absorbed from the specimen, preferably by contacting the treated specimen with a mixture of human anti-Cl-inhibitor, anti-alpha$_2$-macroglobulin and anti-antithrombin III antibodies bound to a solid matrix. The specimen from which the kallikrein-inhibitor complexes have been absorbed is then contacted with monoclonal antibody according to the present invention, which binds to an antigenic determinant of prekallikrein. The amount of material bound by the antibody, that is, the amount of prekallikrein, is measured by standard assay means.

According to another method, levels of prekallikrein, kallikrein-Cl-inhibitor complex, kallikrein-alpha$_2$-macroglobulin complex and kallikrein-antithrombin III complex, may be measured. Samples of a specimen are divided into two aliquots A and B. B is incubated with an excess of a kallikrein inhibitor selected from the group consisting of Cl-inhibitor, alpha$_2$-macroglobulin and antithrombin III to convert all kallikrein in aliquot B to kallikrein-inhibitor complex. The proteins of each of A and B are then separated according to molecular weight. The thus-separated proteins are contacted with a monoclonal antibody of the present invention and the amount of protein bound by the antibody is measured by an assay means. Measuring the amount of about 185 kDa protein from A bound by the antibody indicates the amount of kallikrein-Cl-inhibitor complex in the specimen. Measuring the amount of about 400–1000 kDa protein from A bound by the antibody indicates the amount of kallikrein-alpha$_2$-macroglobulin complex in the specimen. Measuring the amount of about 140 kDa protein from A bound by the antibody indicates the amount of kallikrein-antithrombin III complex in the specimen. Measuring the amount of about 85–88 kDa protein from B bound by the antibody indicates the amount of prekallikrein in the specimen.

In yet another embodiment of the invention, a monoclonal antibody of the invention which recognizes a single antigenic detriment shared by the antigen species kallikrein-Cl-inhibitor complex, kallikrein-alpha$_2$-macroglobulin complex and kallikrein-antithrombin III complex is utilized in a "sandwich" or "double antibody technique". A specimen containing the antigen species is contacted with the immobilized monoclonal antibody to form an immobilized complex of the antigen species and the monoclonal antibody. The immobilized monoclonal antibody-antigen complex is washed to remove unbound protein. The immobilized complex is then contacted with a secondary antibody selected from the group consisting of anti-human Cl-inhibitor antibody, anti-human alpha$_2$-macroglobulin antibody, and anti-human antithrombin III antibody. The amount of antigen bound by the secondary antibody is measured by standard assay means. In this manner, the levels of the kallikrein-inhibitor complexes may be measured.

The antibodies may be bound to an immobilized matrix and used to purify prekallikrein, kallikrein, kallikrein-Cl-inhibitor complex, kallikrein-alpha$_2$-macroglobulin complex or kallikrein-antithrombin III complex, and to generate Prekallikrein-deficient plasma. Matrices of this type charged with prekallikrein may be used to purify high molecular weight kininogen, which binds prekallikrein. Undesirable amounts of prekallikrein or kallikrein may be therapeutically removed from the blood in this manner.

It is accordingly, an object of this invention to provide hybridomas which produce antibodies against human plasma prekallikrein.

Another object of this invention is to provide essentially homogeneous antibodies against this antigen.

It is another object of this invention to provide a method for measuring the level of human plasma prekallikrein in specimens of interest, such as human plasma.

It is an object of this invention to provide a method for measuring the level of human plasma prekallikrein, kallikrein, kallikrein-Cl-inhibitor complex, kallikrein-alpha$_2$-macroglobulin complex and kallikrein-antithrombin III complex in specimens of interest.

It is an object of this invention to provide a method of purifying human plasma prekallikrein.

It is another object of this invention to provide a method for separating the light and heavy chains of kallikrein.

It is an object of the invention to provide an in vivo method for reducing the level of functional kallikrein.

It is an object of the present invention to provide a method of therapy for removing excessive amounts of plasma prekallikrein and kallikrein from the blood.

It is a further object of this invention to provide a method for purifying high molecular weight kininogen.

It is an object of this invention to provide a method for purifying kallikrein-Cl-inhibitor complex.

It is an object of this invention to provide a method for purifying kallikrein-alpha$_2$-macroglobulin complex.

It is an object of this invention to provide a method of purifying kallikrein-antithrombin III complex.

Other objects and advantages of this invention will become apparent from the present disclosure.

Each of the four subject hybridomas are identified herein by the same number assigned to the antibody produced thereby. Thus, for example, the designation "6A6" pertains to both the hybridoma 6A6-B3-E12 and the monoclonal antibody produced by this hybridoma. The particular material referred to, that is, hybridoma versus antibody, is apparent from the context.

The subject hybridomas were deposited in the American Type Culture Collection, 12301 Parklawn Drive, Rockville, Md. 20852, and were given the following ATCC accession numbers: #HB-8863 for 6A6-B3-E12; #HB-8864 for 12H11-F11-B7; #HB-8862 for 13G11-B10-D6; and #HB-8865 for 10B6-F6-D5. #HB8862 and 8863 were deposited on Jul. 9, 1985; #HB-8864 and 8865 were deposited on Jul. 10, 1985.

DETAILED DESCRIPTION OF THE INVENTION

Figure 1:
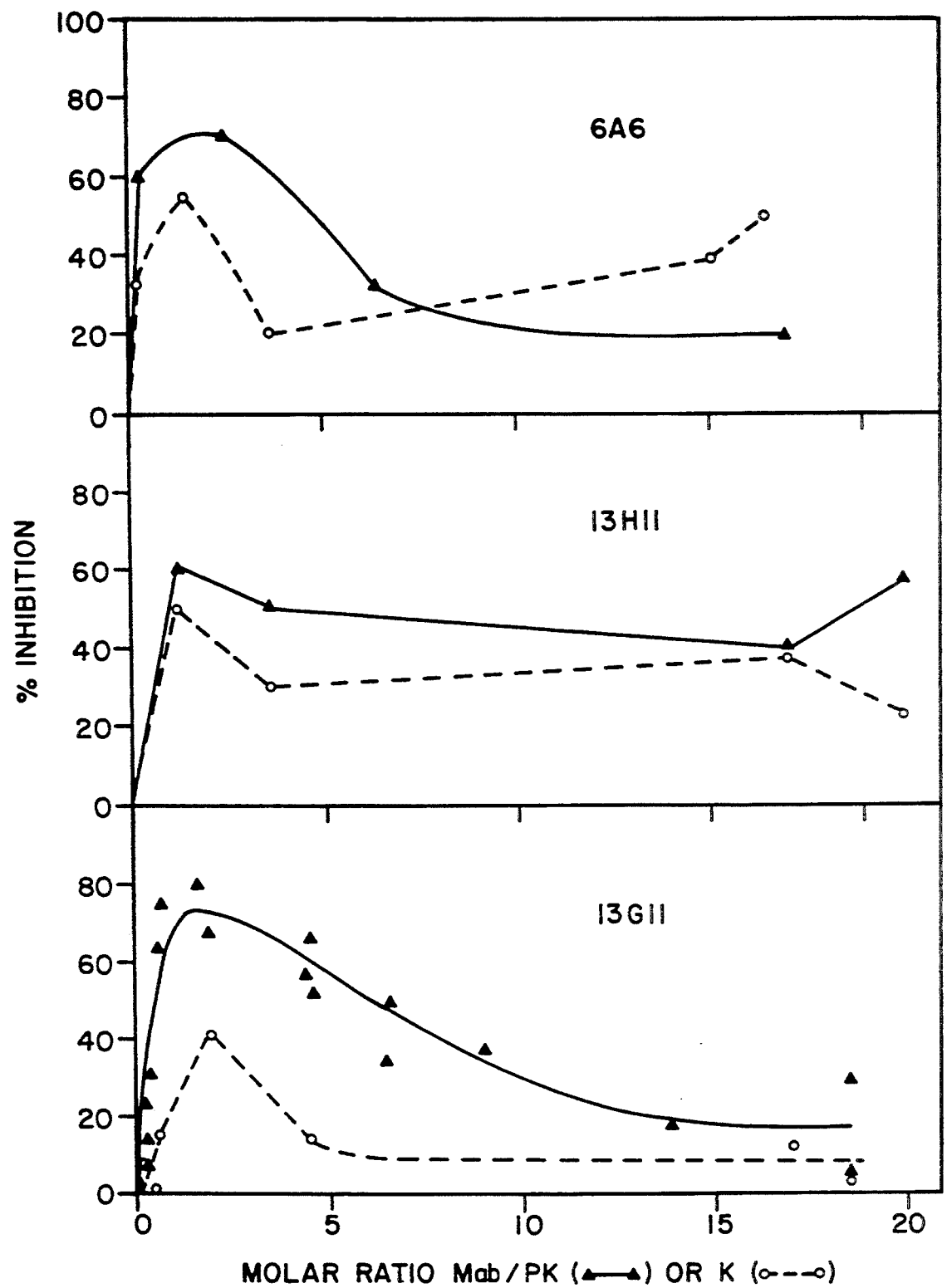
FIG. 1 is a plot of the inhibition of the amidolytic activity of kallikrein (or prekallikrein following activation by factor XIIf) by the antibodies of the present invention as determined by the hydrolysis of the synthetic substrate D-proline-phenylalanine-arginine-p-nitroanilide (D-Pro-Phe-Arg-pNA).

The monoclonal antibodies of the present invention react with human plasma prekallikrein. Monoclonal antibodies produced by one of the four cell lines, 10B6, has not been further characterized. The remaining cell lines, 6A6, 13H11 and 13G11, were found to recognize not only human plasma prekallikrein, but also kallikrein-Cl-inhibitor complex and kallikrein, specifically the heavy chain of kallikrein. The antibody produced by cell line 13G11 also recognizes kallikrein-alpha$_2$-macroglobulin complex, kallikrein-antithrombin III complex, and a complex formed by kallikrein and a mutant of alpha$_1$-antitrypsin ("alpha$_1$-antitrypsin-Pittsburgh") produced by recombinant DNA techniques (Courtney et al., Nature 313. 149 (1985)).

The monoclonal antibodies of the invention produce an IgG monoclonal antibody of subclass IgG$_1$, kappa light chain. The antibodies have a molecular weight of 160 kDa, which upon reduction yield 50 kDa and 28 kDa fragments. They recognize nonreduced human plasma prekallikrein and kallikrein, but reduction with mercaptoethanol decreases the strength of the reaction. Since fewer of the epitopes appear to be available after reduction, binding of antibodies 6A6, 13H11 and 13G11 to the kallikrein heavy chain was observed with large amounts of antigen.

Prekallikrein is present as a collection of microheterogeneous monomer glycoproteins. Each monomer has a molecular weight of 85 kDa or 88 kDa as determined by migration on SDS polyacrylamide gels. The various collections of microheterogeneous monomers have isoelectric points of 7.9, 8.3, 8.6, 8.8, 9.1, 9.3 and 9.5. Hojima et al, J. Biol. Chem. 260, 400 (1985). The species with the isoelectric points 8.6, 8.8, 9.1 and 9.3 are the most abundant.

Human plasma prekallikrein is purified according to a method relying on the difference between isoelectric points, and therefore differences in dissociation constants between prekallikrein and other plasma proteins. The procedure does not eliminate all irrelevant immunoglobulins, but these contaminants can be removed by affinity chromatography, such as by immobilized anti-human IgG chromatography, by protein A chromatography, or by binding with high molecular weight kininogen. Other purification methods may be used, including binding with immobilized monoclonal antibodies according to the present invention.

Mice are immunized with purified human plasma prekallikrein. BALB/c AnSkh mice are preferred, although other strains may be used. The immunization schedule and concentration of antigen administered should be such so as to produced useful quantities of suitably primed splenocytes.

Upon completion of the immunization regimen more completely described below, the mice are sacrificed and their spleens are removed. A suspension of splenocytes in a suitable medium is prepared. Approximately 2.5–5 ml of medium per spleen is sufficient. The protocols for in vitro cell suspension are well established.

The spleen cells are fused with mouse myeloma cells by means of a fusion promotor. The preferred fusion promotor is polyethylene glycol, molecular weight 1300–1600. Other promotors may be used. The mouse myeloma cell line is preferably one of the "drug-resistant" types, to enable selection of hybrids. The most frequently used class of myelomas are the 8-azaguanineresistant cell lines, which are widely known and available. These cell lines lack the enzyme hypozanthine guanine phosphoribosyl transferase and therefore do not survive in "HAT" (hypoxanthine aminopterin-thymidine) medium. The use of myeloma cells with different genetic deficiencies (e.g., other enzyme deficiencies, drug sensitivities, etc.) that can be selected against in media supporting the growth of genotypically competent hybrids is also possible. Additionally, it is preferred that the myeloma cell line does not itself produce any antibody, although in some circumstances, secreting myeloma cell lines may be preferred.

While the preferred fusion promoter is polyethylene glycol of average molecular weight 1300–1600 (available from ATCC), other known fusion promotors may be used.

Fusion of cells may be carried out in an adherent monolayer, such as according to the method described by T. J. McKearn in "Fusion Of Cells In An Adherent Monolayer" *Monoclonal Antibodies: Hybridomas: A New Dimension In Biological Analysis,* (Kennett, R. H., McKearn, T. J., and Bechtol, K. B., eds.), Plenum Press, New York and London, 368–369 (1980). Other fusion techniques may be employed. A cell ratio of 2–3:1 spleen cells per myeloma cell may be used. This ratio may be varied depending on the source of spleen or myeloma cells.

A mixture of unfused myeloma cells, unfused spleen cells and fused cells are distributed for culturing in separate compartments (e.g., the wells of a 96-well microliter plate) in a selective medium in which the unfused myeloma cells will not survive. Distribution of the cells may be by resuspension in a volume of diluent which is statistically calculated to isolate a desired number of cells per compartment. See, McKearn, T. J., "Cloning of Hybridoma Cell Lines by Limiting Dilution in Fluid Phase" in *Monoclonal Antibodies,* p. 374.

When HAT is used as the medium, unfused 8-azaguanine-resistant myeloma cells will not grow. Unfused spleen cells will normally die after a few days, since they are non-malignant. Culturing proceeds for a time sufficient to allow their death. Fused cells continued to reproduce and grow in the selective medium.

The supernatant in each container or compartment having hybrid cell growth is screened and evaluated for the presence of antibody to human plasma prekallikrein. Any suitable antibody-binding detection method may be used, e.g., enzyme-linked immunosorbent assay. Other assays, such as radioimmunoassay, may be advantageously employed.

After selection and cloning, monoclonal antibody to human plasma prekallikrein may be produced by in vitro culturing of the hybridomas or by in vivo peritoneal exudate induction in mice. The first method will yield monoclonal antibody of higher purity. The antibody is recovered from the supernatant essentially free of undesired immunoglobulin. Antibody concentrations of 25–50 micrograms/ml are possible by this method. In growth media containing serum (such as fetal calf serum) a small amount of other immunoglobulins is present.

Where concentrations of antibody larger than those obtained by in vitro culturing of hybridomas are required, the subject hybridomas may be injected into the peritoneal cavity of syngeneic or semi-syngeneic mice. After a suitable period of incubation, the hybridoma causes the formation of antibody-secreting tumors, which will produce 4–10 mg of antibody per ml of blood or peritoneal exudate of the injected mouse. Since mice have normal antibodies in their blood and ascites, a contamination of about 5% from the host mouse is inevitable. Purification of ascites monoclonal antibody may remove these contaminants. The resultant antibody is of high titer, being active at dilutions of 1:300,000 or higher.

The following is one typical procedure for preparing hybrid cell lines according to the present invention, which is not intended to be limited to the same.

Preparation of the Immunogen

Human plasma prekallikrein was purified according the procedure of Scott, et al., Eur. J. Biochem. 100, 77 (1979), with modifications. All operations were carried out in plastic material since glass activates the coagulation system. A total of four units of fresh blood from four healthy human individuals was collected in fractions of 90 ml into tubes containing 10 ml of an anticoagulant solution of 3.8 g of sodium citrate and 2.5 g of dextrose per 100 ml also containing the following proteinase inhibitors: ethylenediamine tetraacetate (0.37 g), benzamidine (0.16 g), aprotinin (3 TIU, Sigma), hexadimethrine bromide (10 mg) and soybean trypsin inhibitor (40 mg). The blood treated in this manner was spun at 2,000 rpm for 10 minutes to separate red cells, and then centrifugated at 10,000 rpm for 20 minutes to separate platelets. The plasma obtained (800 ml) was treated with 0.2 mM (final concentration) of diisopropylfluorophosphate and 3 TIU of aprotinin. The plasma, after addition of 80 mg of hexadimethrine bromide, was stirred for 30 minutes at room temperature with 800 ml of slurry of QAE-Sephadex A-50 (Pharmacia) made by swelling the resin in a buffer containing 0.01M Tris, 0.001M benzamidine, 0.001M ethylenediaminetetraacetate and 0.02% sodium azide adjusted to pH 8 with HCl (buffer A). After stirring, the mixture of plasma-resin was filtered through Whatman No. 1 filter paper. The filtrate was adsorbed to another 800 ml of a QAE-Sephadex slurry made with buffer A and then treated and filtered as above. QAE-Sephadex treatment was repeated again but this time without the hexadimethrine and with 1.5M urea (final concentration). The final filtrate was diluted with water to the conductivity of buffer A and then stirred for 75 minutes at 4° C. with 700 ml of slurry of SP-Sephadex C-50 (Pharmacia) made by swelling the resin with buffer A. The slurry was loaded onto a chromatography column.

Sephadex chromatography, and the operations which followed, were at 4° C., except that protein A/anti-(human IgG) chromatography was at room temperature.

Elution from the Sephadex column was with a linear NaCl gradient from 0 to 0.17M NaCl (800 ml/chamber). Prekallikrein (detected by its coagulant or amidolytic activity as reported by Scott et al., Eur. J. Biochem. 100, 77 (1979)), eluted in partially separated form from most of the plasma proteins, but still contained IgG, factor XI and beta$_2$-glycoprotein I. For separation of these latter two proteins, and for further purifications of prekallikrein from IgG, the pooled prekallikrein-containing fractions of the previous chromatography were concentrated and adjusted to the conductivity of buffer B. Buffer B consisted of 0.1M sodium acetate, 0.1M NaCl, 0.001M ethylenediaminetetraacetate, 0.001 mM benzamidine and 0.02% sodium azide, adjusted to pH 5.3 with acetic acid. The eluate of the first SP-Sephadex chromatography after the above adjustment was applied to a second SP-Sephadex column (about 300 ml bed volume) equilibrated with buffer B. Elution was with a linear gradient 0 to 0.35M NaCl in buffer B (400 ml/chamber). The fractions containing prekallikrein (factor XI should be absent) were pooled, concentrated and stored at −70° C.

For removal of the remaining IgG contaminants, aliquots (1 to 2 ml) of the concentrated fractions were adjusted to pH 8 with 1M Tris and then applied to a protein A-Sepharose column (3 ml bed volume) placed in tandem with an anti-(human-IgG)-agarose column (6 ml bed volume). Elution of pure prekallikrein was with 10 mM Tris-HCl/0.15M NaCl, pH 7.5, as the buffer. Prekallikrein thus purified can be stored at −70° C. for at least three years.

Immunization

Four male or female BALB/c AnSkh mice, 8–10 weeks old (Temple University, Skin and Cancer Hospital,) were immunized subcutaneously with 35 micrograms of protein/mouse in complete Freund's adjuvant (week 0) and then again subcutaneously with 35 micrograms of protein/mouse in incomplete Freund's adjuvant at week 5. Blood was removed and screened at week 7 for antibodies to the immunogen using enzyme-linked immunosorbent assay ("ELISA"). At week 11, 50 micrograms of immunogen/mouse in 0.15M sodium chloride were intraperitoneally injected. Four days later, blood was removed from the retro-orbital plexus of each mouse under light anesthesia, and the two strongest positive mice were selected as spleen donors. The spleens of these animals were aseptically removed and placed in tissue cultured dishes (15×60 mm) containing Hank's balanced salt solution ("HBSS", Gibco, Grand Island, N.Y.) to which 50 micrograms/ml of gentamycin or "PEN/STREP" (Gibco) were added. The latter is a mixture of penicillin and streptomycin. The spleens were then transferred into other culture dishes containing HBSS. The spleens were teased apart with sterile forceps and then transferred into a centrifuge tube which was placed in ice for two minutes to allow debris to settle. The cell-suspension was transferred into another centrifuge tube and spun for ten minutes at 1200 rpm. After discarding the supernatant, the cells were resuspended in 5–10 ml of 0.17M NH$_4$Cl (ice cold) and placed in ice for five minutes with occasional mixing in order to lyze red blood cells. The cell suspension was gently underlaid into 10 ml of 1:1 dilution of HBSS:normal serum and centrifuged at 1200 rpm for ten minutes. Fetal calf serum ("FCS") may be used as the normal serum. The cells were then washed thrice in Dulbeco's Modified Eagle's Medium ("DME", Gibco). The number and viability of cells was then determined.

SP2/O-Ag14 myeloma cells used in the hybridization procedure were washed in the same way as the unlyzed splenocytes.

Preparation of Splenocyte Feeder Layers

On the day of fusion, non-immune splenocytes from the same mouse strain as immunized above were processed according to the same procedure as above without immunization and without washing in DME. These non-immune splenocytes were used to prepare feeder layers as follows. The non-immune cells were resuspended in DME+HAT+20% FCS to a density of 2–4×10$^6$ cells/ml. These cells were seeded onto 96-well plates (1–2×10$^5$ cells/well) and incubated in 5% CO$_2$ at 37° C. overnight as a sterility check before plating out hybrid cells.

Hybridization

Fusion was carried out as follows. 1.5 ml of immune splenocytes and 1.5 ml of SP2/O-Ag14 cells were pipeted onto a concanavalin A-coated plate. The cell concentration of each cell type was adjusted so that the ratio of splenocytes to SP2/O-Ag14 cells was 2–3:1, with a total of 7–10×10$^7$ cells/plate. The plates were then incubated in 5% CO$_2$ at 37° C. for 45–60 minutes to allow for attachment of the cells to concanavalin A. Fusion was performed by adding 1 ml of a 50% DME:PEG solution to each plate, drop by drop. The plates were left standing for 15 seconds after the addition of the first drop. The cells were then washed twice with 5 ml of DME. Following addition of 5 ml of DME+20% FCS/plate, the cells were incubated overnight.

Selection and Growth of Hybridomas

Following overnight incubation, the cells from the above hybridization procedure were transferred into centrifuge tubes and spun at 1500 rpm for 15 minutes. The supernatants were discarded. The cells from each tube were suspended in 40–45 ml of DME+HAT+20% FCS and transferred into the 96-well plates (0.1 ml cell suspension/well containing non-immune splenocyte feeder layers as prepared in "Preparation of Splenocyte Feeder Layers", see above). The plates were cultured with 10% CO$_2$ at 37° C. in a humid atmosphere. The cells were allowed to grow for 3–5 days, after which an additional 0.1 ml of DME+HAT+20% FCS were added to each well. Hybrids were checked daily. Three to four weeks after fusion, the cells were switched to DME+HAT+10% FCS (no aminopterin). Hybridoma cultures with antibody reactive to the immunogen were selected and cloned by a limiting dilution technique. McKearn, T. J. "Cloning of Hybridoma Cells by Limiting Dilution and Fluid Phase" in *Monoclonal Antibodies*, p. 374. Cells from the four strongest positive cultures were injected intraperitoneally (about 2×10$^6$ cells in 0.5 ml PBS/mouse) into four BALB/c mice which had been primed 10–14 days previously with 0.5 ml of pristane (2,6,10,14-tetramethyl-pentadecane). The cultures were designated 6A6, 13H11, 13G11, and 10B6. After 7–14 days, the blood was removed from the retro-orbital plexus of each mouse under light ether anesthesia and the tumor-induced ascites fluid was harvested. The antibody titer of 6A6, 13H11 and 13G11 was determined in the ascites fluid using pure immunogen and ELISA.

Purification of Antibody

Antibodies were purified from the ascites fluids and assayed as follows. Fluids were desalted with a desalting gel filtration column (Sephadex G-25) using a buffer of 20 mM Tris-HCl pH 7.8. The protein-containing fraction eluted from this column was applied to a "MONO-Q" ion exchange column (Pharmacia) which was adapted to a fast protein liquid chromatography machine (Pharmacia). The antibody was eluted by a step gradient generated by buffer A (20 mM Tris-HCl, pH 7.8) and buffer B (20 mm Tris-HCL, pH 7.8, +1.0M NaCl). Programming was planned to give an isocratic elution of the desired monoclonal antibody. The antibody was detected with mouse anti-IgG by Outcherlony immunodiffusion. The positive fractions were rechromatographed by the same technique, except that the buffers were pH 7.5. Rechromatography yielded a microheterogeneous peak of the desired antibody. Further rechromatography under chromatofocusing conditions, pH 7-4, gave only one microheterogenous peak for 6A6, 13H11, or 13G11, with elution pH's for each antibody as shown in Table 1. The sub-class of the monoclonal antibodies was determined with a mouse immunoglobulin subtype identification kit (Mannheim Boehringer).

TABLE 1

| Clone | ATCC No. | Clone Titer | Antibody Sub-class | Chromatofocusing pH elution |
|---|---|---|---|---|
| 6A6 | HB-8863 | >300,000 | IgG$_1$, kappa | 5.66 |
| 13H11 | HB-8864 | 300,000 | IgG$_1$, kappa | 5.56 |
| 13G11 | HB-8862 | >300,000 | IgG$_1$, kappa | 5.76 |
| 10B6 | HB-8865 | — | IgG$_1$, kappa | — |

The specificity of the monoclonal antibody 13G11 for prekallikrein and for kallikrein (with or without separation of the two polypeptide chains by mercaptoethanol) was demonstrated either by applying the proteins directly to the nitrocellulose membrane, or after separation of the proteins by 10% SDS-PAGE according to Laemmli, Nature 227, 680 (1970) and electrophoretic transfer to nitrocellulose membranes according to Towbin, et al., Proc. Natl. Acad. Sci. U.S.A. 76, 4350 (1979). Binding of antigen by antibody 13G11 was detected by ELISA, using peroxidase-conjugated goat-antimouse IgG as the secondary antibody. The results are set forth in Table 2.

TABLE 2

| Protein | Direct Application | Electrophoretic Transfer from SDS-PAGE Non-Reduced | Electrophoretic Transfer from SDS-PAGE Reduced |
|---|---|---|---|
| H. Plasma PK | + | +a | — |
| H. Plasma K | + | +a | |
| H. Plasma K (heavy chain) | | | +a |
| H. Plasma K (light chain) | | | —a |
| B. Pancreas K | | —b | |
| B. Plasma K | | — | |
| H. Plasma factor XI | | — | |
| H. Plasma factor XII | — | — | |
| H. Plasma HMWK | — | — | |

H = Human
B = Bovine
PK = Prekallikrein; K = Kallikrein; HKWK = high molecular weight kininogen
+ = positive immunoreaction
— = negative immunoreaction
a = antibodies 6A6 and 13H11 were also tested, and the reaction was the same as that of 13G11
b = antibody 6A6 was also tested, and reaction was the same as that of 13G11.

The four monoclonal antibodies of the present invention all reacted with biochemically pure plasma prekallikrein. The three monoclonal antibodies 6A6, 13H11 and 13G11 were also positive against plasma kallikrein and its heavy chain. Although fewer of the epitopes appeared to be available after reduction of both prekallikrein and kallikrein with mercaptoethanol, binding of antibody 6A6, 13H11 and 13G11 to the kallikrein heavy chain was observed using 10-fold as much kallikrein as compared to binding under non-reducing conditions.

Table 2 indicates the specificity of the antibodies for prekallikrein and kallikrein purified from plasma. The antibodies recognize plasma kallikrein and do not cross-react with kallikrein derived from tissue; nor do they cross-react with the related plasma proteins factor XI, factor XII and high molecular weight kininogen. Specificity for prekallikrein, kallikrein, kallikrein-C1-inhibitor complex, kallikrein-alpha$_2$-macroglobulin complex and kallikrein-antithrombin III complex was observed for 13G11 by separation of proteins in normal plasma (and proteins in prekallikrein-deficient plasma to which kallikrein was added) or normal plasma activated on a surface, by SDS-PAGE and immunoblotting. The kallikrein-inhibitor complexes formed upon activation of the normal plasma were indistinguishable from those formed from purified proteins.

The effect of the instant monoclonal antibodies on the amidolytic activity of prekallikrein and kallikrein was determined from the hydrolysis of the chromogenic substrate D-Pro-Phe-Arg-pNA in pure systems, as follows:

0.3 micrograms of either prekallikrein or kallikrein in 50 microliters of buffer (pH 7.5) containing 1 mg/ml of human serum albumin were incubated at 37° C. for 40 minutes with monoclonal antibody in ratios of antibody to prekallikrein (or kallikrein) varying from zero to 15. Where prekallikrein was used, it was activated by factor XIIf after incubation with the monoclonal antibody. Kallikrein was prepared from prekallikrein by activation with factor XIIf, followed by inactivation of the activated fragment with corn trypsin inhibitor. The amidolytic activity of the plasma protein in the presence or absence of monoclonal antibody was determined spectrophotometrically at 405 nm in 10 microliter aliquots added to 0.3 ml of a 1 mM solution of the chromogenic substrate made in 0.1M of sodium phosphate/0.15M NaCl, pH 7.6, prewarmed at 37° C. The results appear in FIG. 1. The antibody concentration is as indicated in FIG. 1.

Figure 2:
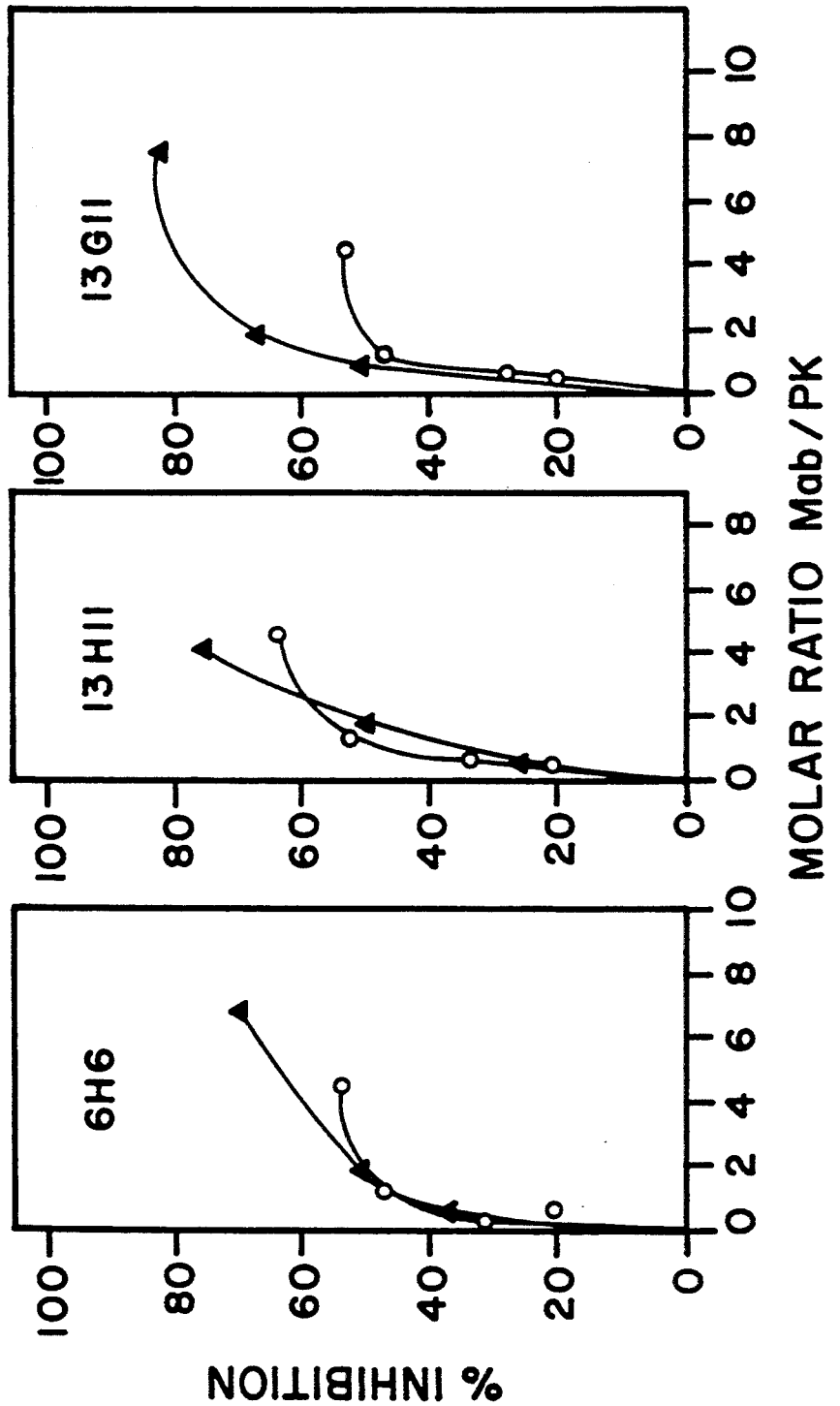
FIG. 2 is a plot of the inhibition of kaolin activation of human plasma by the antibodies of the present invention as determined by the hydrolysis of the synthetic substrates D-Pro-Phe-Arg-pNA or benzoyl-proline-phenylalanine-arginine-p-nitroanilide (Bz-Pro-Phe-Arg-pNA).

Likewise, the effect of the present monoclonal antibodies on the amidolytic activity of prekallikrein and kallikrein in normal human plasma was determined from the hydrolysis of D-Pro-Phe-Arg-pNA or Bz-Pro-Phe-Arg-pNA. Normal plasma was incubated with or without (control) monoclonal antibody followed by activation with 20 micrograms of kaolin. The antibody concentration is as indicated in FIG. 2, assuming 25 micrograms of prekallikrein per ml of normal plasma. In the case of plasma, equilibrium with the antibodies was already reached after 5 min. of incubation.

FIGS. 1 and 2 demonstrate that low concentration of monoclonal antibody 6A6, 13H11, and 13G11 affect the function of prekallikrein and kallikrein. Incubation of these monoclonal antibodies with normal plasma in a molar ratio of antibody to prekallikrein up to 5:1 decreased hydrolysis of the two chromogenic substrates tested with a profile slightly different for each antibody (FIG. 2). When either kallikrein or prekallikrein was incubated with these antibodies, followed by activation of prekallikrein with factor XIIf, inhibition was maximal at a molar ratio of antibody to antigen of 1 to 5, and decreased with high concentrations of antibody (FIG. 1). Inhibition patterns were slightly different for the three antibodies.

The amidolytic activity of kallikrein demonstrated above with chromogenic substrates is a function of the enzyme's protease activity. Protease activity is present in the light chain. Inhibition as indicated above demonstrates that the epitope recognized by the monoclonal antibodies of the present invention, although located on the heavy chain, is sterically close to the protease active center.

Figure 3:
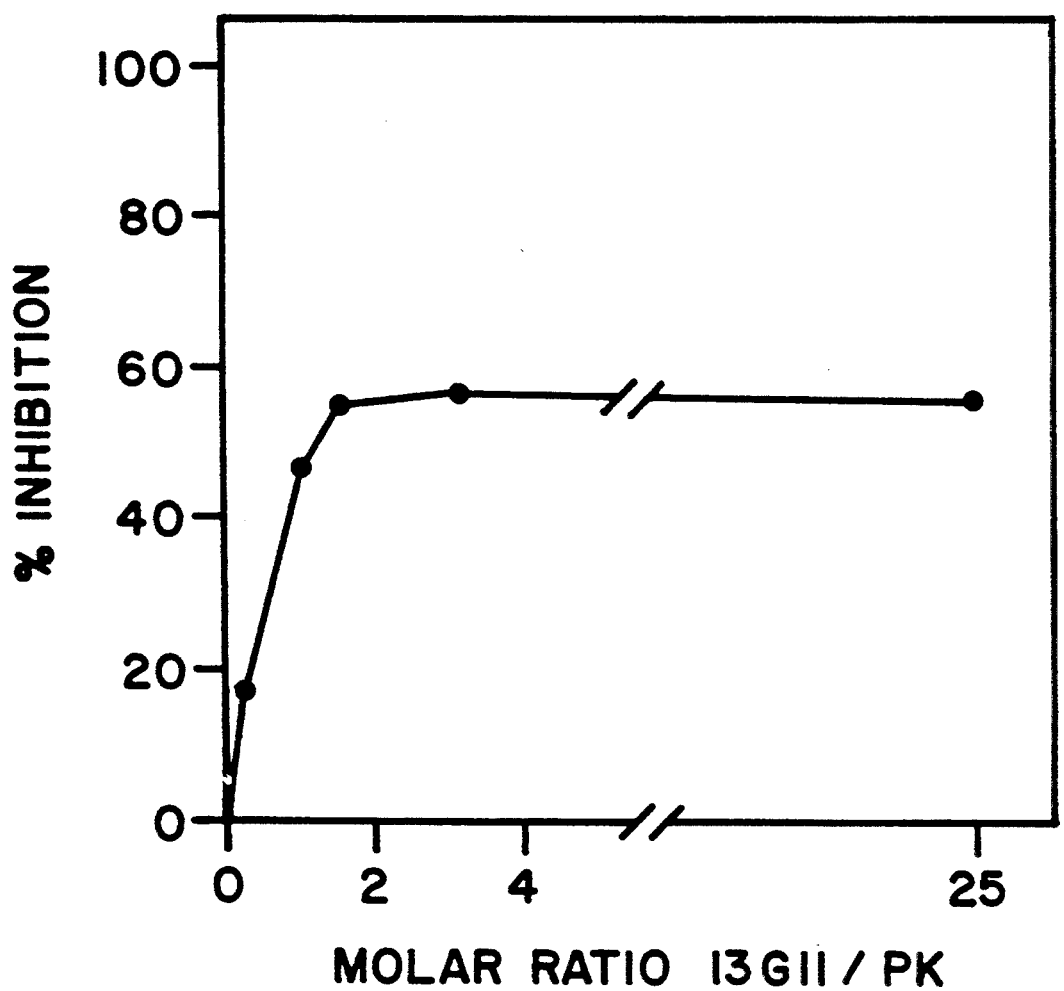
FIG. 3 is a plot of the inhibition of the procoagulant activity of prekallikrein in plasma with the antibody 13G11. Similar patterns were observed with the 6A6 and 13H11 antibodies.

The effect of the monoclonal antibodies of the present invention on the procoagulant activity of prekallikrein was determined. This activity involves both heavy and light chains. Prekallikrein was incubated with each of antibodies 6A6, 13H11 and 13G11 for 30 minutes at 37° C. Thereafter, the prekallikrein was added to prekallikrein-deficient plasma and assayed for clot formation according to the method of Proctor et al., Am. J. Clin. Pathol. 35:212–219 (1961). FIG. 3 shows the inhibition curve for antibody 13G11. It is apparent that procoagulant activity was decreased by about 60% when prekallikrein was incubated with equimolar concentrations of monoclonal antibody before addition to prekallikrein-deficient plasma.

The effect of the instant monoclonal antibodies on kallikrein cleavage of factor XII was established by incubating factor XII, kallikrein and antibody 13G11 at antibody concentrations of 0 to 10 micrograms in a final volume of 40 microliters, pH 7.7. Activation of factor XII was assayed with a chromogenic substrate. The results indicate that antibody 13G11 inhibited activation of factor XII of kallikrein with a pattern similar to that observed for kallikrein in FIG. 1.

The effect of antibody 13G11 on cleavage of prekallikrein by factor XII activated with kaolin in the presence of high molecular weight kininogen, a purified system which mimics the plasma contact activation, was determined by hydrolysis of the substrate D-Pro-Phe-Arg-pNA. The strongest inhibition of hydrolysis of the synthetic substrate was when both prekallikrein and high molecular weight kininogen were present, suggesting a conformational change in the prekallikrein structure, upon binding to high molecular weight kininogen for the formation of a better substrate for the surface-activated factor XII.

The monoclonal antibodies of the present invention are useful in detecting changes in the concentration of prekallikrein, kallikrein, kallikrein-Cl-inhibitor complex, kallikrein-alpha$_2$-macroglobulin complex and/or kallikrein-antithrombin III complex in human plasma. Thus, the antibodies may be used to diagnose activation of the contact coagulation system, which is signalled by changes in the level of these proteins or protein complexes.

Under normal conditions, essentially only prekallikrein is present in plasma. However, under conditions in which the contact activation system is activated, as for example in the presence of endotoxin, there is a decrease in the level of prekallikrein with a concomitant increase in the levels of kallikrein and/or kallikrein-Cl-inhibitor complex, kallikrein-alpha$_2$-macroglobulin complex and kallikrein-antithrombin III complex. At a constant temperature, e.g. 37° C., the distribution of kallikrein among the inhibitors depends on the affinity of kallikrein for each inhibitor, and on the concentration of active inhibitors present in plasma.

The following are two methods for measuring the levels of prekallikrein, kallikrein, kallikrein-Cl-inhibitor complex, kallikrein-alpha$_2$-macroglobulin complex and kallikrein-antithrombin III complex. One method utilizes immunoblotting, followed by enzyme-linked immunosorbent assay or radioimmunoassay. Another method employs the so-called "sandwich" assay.

Measurement Of Prekallikrein, Kallikrein, Kallikrein-Cl-Inhibitor Complex, Kallikrein-Alpha$_2$-Macroglobulin Complex, And Kallikrein-Antithrombin III Complex Plasma is obtained from a small volume of blood (e.g. 2 ml) as described above under "Preparation of the Immunogen", except that no inhibitors are used, and centrifugation is with a Fisher micro-centrifuge, Model 235A for 2 minutes. Aliquots of 5 microliters of plasma thus obtained and aliquots of 5 microliters of commercially available prekallikrein-deficient plasma (e.g., George King Biomedicals, Overland Park, Kans.) are prepared. (Alternatively, prekallikrein-deficient plasma may be prepared from normal pooled plasma by affinity chromatography with immobilized monoclonal antibody of the present invention, which antibody binds prekallikrein). Quintuplicate samples from each plasma are prepared in this manner, except that 2.0 micrograms of purified human Cl-inhibitor are added to one of the quintuplicate aliquots, 10.0 micrograms of purified alpha$_2$-macroglobulin to another of the quintuplicate aliquots, 2.0 micrograms of purified antithrombin III added to another of the quintuplicate aliquots, and 2.0 micrograms of purified "alpha$_1$-antitrypsin-Pittsburgh" to yet another of the quintuplicate aliquots (incubation time 20 min. in each instance). Alpha$_1$-antitrypsin-Pittsburgh is an analogue of alpha$_1$-antitrypsin which is prepared by recombinant DNA techniques. It strongly binds kallikrein.

The samples are electrophoresed as described in Lamelli, Nature 227, 680 (1970), simultaneously with molecular weight standards. The electrophoresed proteins are electrophoretically transferred to nitrocellulose sheets (Schleicher and Schuell), 0.45 micrometer pore size, at 8 V/cm for 16–20 hr, 4° C. according to Burnette, Anal. Biochem. 112, 195 (1981). The nitrocellulose sheets, after brief washing with 10 mM Tris-HCl buffered to pH 7.5 containing 0.15M NaCl (TBS), are incubated with TBS containing 5% casein (TBS-C) for 2 hr at 24° C., followed by incubation with the 13G11 monoclonal antibody (0.8 microgram/ml TBS-C) for 2 hours. The protein blot is washed with four changes of TBS-C containing 0.05% Nonidet P-40, and then incubated with goat anti-mouse IgG conjugated with horseradish peroxidase (0.040 purpurogallin units/ml, Sigma). The protein blots are washed as previously with an additional washing with TBS and then placed in a solution of TBS/methanol (100 ml/20 ml) containing 0.015% H$_2$O$_2$ and 0.05% 4-chloro-1-naphthol for 15–30 min., to detect the peroxidase-conjugated IgG. Staining is measured by scanning densitometry.

Alternatively, the 13G11 monoclonal antibody used in the incubation may be labeled with, e.g., iodine-125. Detection of the proteins containing the epitope recognized by the monoclonal antibody is by autoradiography and densitometry.

In non-activated normal plasma, only two stained bands are observed corresponding to the 88- and 85-kDa prekallikrein species. The staining intensity as measured by densitometry is proportional to the amount of prekallikrein contained in the sample. In plasma in which prekallikrein has been activated, the presence of kallikrein-Cl-inhibitor complex is likewise visualized by a stained band at the position corresponding to the molecular weight of the complex, 185 kDa. The presence of kallikrein-alpha$_2$-macroglobulin complex is visualized by various stained bands at positions corresponding to the molecular weight of the complex, 400–1000 kDa. The presence of kallikrein-antithrombin III complex is visualized by a stained band at the position corresponding to the molecular weight of the complex, 140 kDa. For the aliquot to which alpha$_1$-antitrypsin-Pittsburgh has been added, the band at about 125 kDa corresponds to kallikrein-alpha$_1$-antitrypsin-pittsburgh complex. In prekallikrein-deficient plasma, scanning densitometry of the bands at positions corresponding to molecular weights of 85–88 kDa, 185 kDa, 400–1000 kDa and 140 kDa measures non-specific bound 13G11 monoclonal antibody or secondary antibody.

When high amounts of the active enzyme kallikrein are present, as in activation of the contact system under conditions in which the inhibitors are inactivated, the intensity of the stained band corresponding to kallikrein-Cl-inhibitor complex will be increased upon addition of exogenous Cl-inhibitor, with the increase being proportional to the amount of kallikrein present in the sample. Likewise the intensity of the stained band corresponding to kallikrein-alpha$_2$-macroglobulin complex and kallikrein-antithrombin III complex will be increased upon addition of exogenous alpha$_2$-macroglobulin or antithrombin III, respectively. The increase is proportional to the amount of kallikrein present in the sample.

For quantitation, the above procedure is repeated with the same monoclonal antibody, using known amounts of purified prekallikrein, purified kallikrein-Cl-inhibitor complex (known amounts of kallikrein incubated with a molar excess of Cl-inhibitor for 20 min. at 24° C.), purified kallikrein-alpha$_2$-macroglobulin complex (known amounts of kallikrein incubated with a molar excess of alpha$_2$-macroglobulin for 20 min. at 24° C.), purified kallikrein-antithrombin III complex (known amounts of kallikrein incubated with a molar excess of antithrombin III for 20 minutes at 24° C.) purified kallikrein-alpha$_1$-antitrypsin-Pittsburgh complex (known amounts of kallikrein incubated with a molar excess of alpha$_1$-antitrypsin Pittsburgh for 20 minutes at 24° C.) as standards. These standards, which may span the range from 0.025 to 2.5 micrograms of prekallikrein and from 5 to 100 nanograms of kallikrein-Cl-inhibitor, kallikrein-alpha$_2$-macroglobulin, kallikrein-antithrombin III or kallikrein-alpha$_1$-trypsin Pittsburgh complexes, are added to a 5 microliter volume of prekallikrein-deficient plasma. A standard curve of staining intensity (as measured by scanning densitometry) versus concentration may then be prepared for each band.

The amounts of prekallikrein, kallikrein-Cl-inhibitor complex, kallikrein-alpha$_2$-macroglobulin complex and kallikrein-antithrombin III complex in the sample are derived as follows:

For aliquots of sample receiving no exogenous Cl-inhibitor, alpha$_2$-macroglobulin or antithrombin III, the intensity of the 88- and 85-kDa bands is proportional to the total concentration of prekallikrein plus kallikrein. The intensity of the 185 kDa band is proportional to the concentration of kallikrein-Cl-inhibitor complex. The intensity of the band at about 400–1,000 kDa is proportional to the amount of kallikrein-alpha$_2$-macroglobulin complex. The intensity of the band at about 140 kDa is proportional to the amount of kallikrein-antithrombin III complex.

In those aliquots to which exogenous Cl-inhibitor, alpha$_2$-macroglobulin, antithrombin III, or any combination thereof, is added, any available kallikrein becomes complexed with these inhibitors. The remaining band intensity of 88 or 85 kDa is thus a measure of the concentration of prekallikrein alone.

In those aliquots to which alpha$_1$-antitrypsin-Pittsburgh is added, any available kallikrein becomes complexed with this inhibitor. The intensity of the band at about 125 kDa is proportional to the kallikrein-alpha$_1$-antitrypsin-Pittsburgh complex. Kallikrein concentrations are calculated by comparison of the intensity of the band at about 125 kDa with the intensities of standards of kallikrein-alpha$_1$-antitrypsin-Pittsburgh complex formed from known amounts of kallikrein.

While the measurement of prekallikrein, kallikrein, kallikrein-Cl-inhibitor complex, kallikrein-alpha$_2$-macroglobulin complex and kallikrein-antithrombin III complex, has been exemplified using an immunoblotting procedure followed by enzyme-linked immunosorbent assay, more accurate measurements are possible by further labelling the enzyme-conjugated secondary antibody, or labeling the 13G11 monoclonal antibody, with an appropriate radiolabel, such as iodine-125. Radiolabelling with iodine-125 is most advantageously conducted to a specific activity of about $10^7$ cpm/nanomol. Appropriate methods for radiolabelling immunoglobulins are known to those skilled in the art, e.g., Helmkamp et al., Int. J. Appl. Radiat. Isotopes 18, 737 (1967). Radiometric measurement of the excised bands located by the above staining procedure provides a more accurate determination of protein concentration than scanning densitometry alone.

The procedure is most advantageously performed using minielectrophoresis and miniblotting apparatus, with incubation of the electrophoresed gels with TBS-C and monoclonal antibody-containing solution, each for 45 minutes at 37° C. Quantitation of prekallikrein, kallikrein, kallikrein-Cl-inhibitor complex, kallikrein-alpha$_2$-macroglobulin complex, and/or kallikrein-antithrombin III complex can thus be efficiently achieved between 3 to 4 hours. The duration of the assay can be reduced without diminishing its sensitivity by the use of labelled or enzyme-conjugated primary antibody. Conjugation of antibodies to enzymes is well known to those skilled in the art. See, for example, *Methods In Enzymology*, 73, 147 (1981).

Measurement of kallikrein can alternatively be achieved by incubating the specimen with an excess of a labelled (e.g. iodine-125) kallikrein inhibitor i.e., Cl-inhibitor, alpha$_2$-macroglobulin or antithrombin III, separation of the proteins by molecular weight as above, and immunoblotting with a monoclonal antibody of the invention conjugated to an enzyme which is used to locate the radiolabelled kallikrein-inhibitor complexes. The amount of radiolabelled kallikrein-inhibitor complex formed is proportional to the amount of kallikrein in the sample.

While the above method has been exemplified using electrophoresis to separate the component proteins of the specimen of interest prior to immunoreaction with monoclonal antibody, it is contemplated that other appropriate means for separating proteins according to molecular weight may be advantageously substituted, e.g., gel filtration, thin layer chromatography, differential centrifugation, sucrose gradient density centrifugation, etc.

Quantitation of prekallikrein, kallikrein, kallikrein-Cl-inhibitor complex, kallikrein-alpha$_2$-macroglobulin complex, and/or kallikrein-antithrombin III complex in specimens may also be advantageously conducted without separating the component proteins by electrophoresis, according to the so-called "sandwich" or "double antibody" technique.

The complexes of kallikrein-Cl-inhibitor, kallikrein-alpha$_2$-macroglobulin or kallikrein-antithrombin III are directly measured utilizing available antibodies to Cl-inhibitor, alpha$_2$-macroglobulin and antithrombin III, in conjunction with a monoclonal antibody of the present invention, which monoclonal antibody is immobilized by binding to a solid phase. Such binding may be, for example, to the wells of a microtiter plate, or to beads.

Monoclonal antibodies to Cl-inhibitor (e.g. antibody "4C3" produced as described in *Proc. Nat.l Acad. Sci. USA* 82, 5190 (1985)) may be used in the herein double-antibody technique.

A series of standard solutions is first prepared containing kallikrein-Cl-inhibitor complex ranging from 3 nanograms to 50 nanograms. Likewise, series of standard solutions containing kallikrein-alpha$_2$-macroglobulin complex (5 nanograms to 100 nanograms) and kallikrein-antithrombin III complex (3 nanograms to 50 nanograms) are prepared. To each standard solution should be added prekallikrein-deficient plasma in a volume equal to that of the plasma sample to be analyzed.

According to the double .antibody method for directly measuring the complexes of kallikrein-Cl-inhibitor, kallikrein-alpha$_2$-macroglobulin, or kallikrein-antithrombin III, the specimen for which the amount of complex is to be determined is diluted with, e.g., 10 mM Tris-HCl/150 mM NaCl (pH 7.5) to a convenient dilution.

The diluted specimen is then contacted with an immobilized monoclonal antibody of the invention at 37° C. for one hour to form an immobilized monoclonal antibodyantigen complex of the monoclonal antibody and the antigen species which may be present in the specimen (kallikrein, prekallikrein, kallikrein-Cl-inhibitor complex, kallikrein-alpha$_2$-macroglobulin and kallikrein-antithrombin III complex). The monoclonal antibodies of the invention may be conveniently immobilized by fixing to the wells of a microtiter plate (e.g., from Biomed, Inc.). Methods for binding antibodies to substrates are well-known to those skilled in the art. For fixing to a microtiter plate, the monoclonal antibody (about 3 micrograms per plate well) may be mixed with 200 microliters of 50 mM sodium carbonate/sodium bicarbonate (pH 9.6). Binding sites on the plate which have not bound antibody may be blocked with 5% bovine serum albumin.

Following incubation of the specimen with monoclonal antibody of the invention to bind antigen, the microtiter plates, to which is immobilized monoclonal antibody-antigen complex, are washed according to standard methods to remove unbound protein (e.g., with 10 mM Tris-HCl/150 mM NaCl, pH 7.5, containing 5% bovine serum albumin). An appropriately labelled secondary antibody is then added to the wells containing the immobilized monoclonal antibody-antigen complex and incubated at 37° C. for one hour. Thus, it is readily appreciated that where kallikrein-Cl-inhibitor complex is to be measured, the secondary antibody comprises anti-human-Cl-inhibitor antibody. Where kallikrein-alpha$_2$-macroglobulin complex or kallikrein-antithrombin III complex are to be measured, the secondary antibody comprises anti-human alpha$_2$-macroglobulin antibody or anti-human-antithrombin III antibody, respectively.

Labeling of the secondary antibody is most effectively carried out with an enzyme, e.g., alkaline phosphatase, so that the binding of the secondary antibody to the antigen may be measured by enzyme-linked immunosorbent assay.

The amount of each kallikrein-inhibitor complex bound by the relevant secondary antibody (e.g., the amount of kallikrein-Cl-inhibitor complex bound by anti-human-Cl-inhibitor antibody) is readily determined by comparison to the standard solutions prepared above containing known amounts of the kallikrein-inhibitor complex (e.g., kallikrein-Cl-inhibitor complex). The bound material is measured by standard assay methods. Such methods include, but are not limited to, immunological assay methods such as enzyme-linked immunosorbent assay, radioimmunoassay, fluorescent assay, precipitation, agglutination, and electroimmunodiffusion. Such methods also include fast liquid chromatographic methods such as ion exchange, gel filtration and reverse phase chromatography. Assay of the specimen in this manner indicates the amount of complex present in the specimen. When the secondary antibody is labelled by conjugation to an enzyme, an enzyme-linked immunosorbent assay is employed.

In a similar manner, the amount of kallikrein in a specimen may be determined by utilizing a kallikrein ligand (that is, a protein which binds kallikrein) selected from the group consisting of alpha$_1$-antitrypsin-Pittsburgh, Cl-inhibitor, alpha$_2$-macroglobulin and antithrombin III. Appropriately labelled, such a ligand may be used in a manner analogous to the above-described secondary antibodies to determine the amount of kallikrein in the specimen. Accordingly, the specimen is incubated with an excess of the labelled ligand, which binds with the available kallikrein to form a labelled kallikrein-ligand complex, e.g. labelled kallikrein-alpha$_1$-antitrypsin-Pittsburgh complex. By "excess" is meant an amount of ligand sufficient to convert all kallikrein in the specimen to kallikrein-ligand complex. The specimen is then contacted with an immobilized monoclonal antibody of the invention, which recognizes an antigenic determinant of kallikrein. The labelled material bound by the antibody is measured by any of the same standard assay means as abovementioned. The amount of kallikrein bound by the labelled ligand may be determined by comparison to standard solutions. For this purpose, a series of standard solutions is prepared containing known amounts of labelled kallikrein-ligand complex prepared from known amounts of kallikrein. Where alpha$_1$-antitrypsin-Pittsburgh is the ligand, for example, standard solutions containing labelled kallikrein-alpha$_1$-antitrypsin-Pittsburgh complex ranging from 3 nanograms to 50 nanograms are advantageously employed. To each standard solution should be added prekallikreindeficient plasma in a volume equal to that of the plasma sample to be analyzed.

The double-antibody method may be employed in conjunction with the monoclonal antibodies of the invention to simultaneously measure two or more of the hereindescribed antigen species (prekallikrein, kallikrein, kallikrein-Cl-inhibitor complex, kallikrein-alpha$_2$-macroglobulin complex, kallikrein-antithrombin III complex) by the simple expedient of dividing the specimen sample into two or more aliquots.

Where all five antigen species are to be measured, the sample is divided into five aliquots, A, B, C, D and E. Aliquot B is incubated with labelled alpha$_1$-antitrypsin-Pittsburgh. The thus-treated aliquot B and the aliquots C, D and E are advantageously added to separate wells of a microtiter plate, to which monoclonal antibody of the present invention has been bound. Following incubation and washing as described above, the following are then added to the respective wells containing the aliquots: To aliquot C is added labelled anti-human-Cl-inhibitor antibody. To aliquot D is added labelled anti-human-alpha$_2$-macroglobulin antibody. Labelled anti-human antithrombin III antibody is added to aliquot E. The amounts of kallikrein, kallikrein-Cl-inhibitor complex, kallikrein-alpha$_2$-macroglobulin complex and kallikrein-antithrombin III complex in the specimen are then determined by standard assay means from aliquots B through E.

The aliquot A, after convenient dilution in 0.05M sodium carbonate (pH 9.6), is bound to separate wells of a microtiter plate. Standard solutions made of purified prekallikrein (1 to 100 nanograms), each containing prekallikrein-deficient plasma in a volume equal to that of the diluted aliquot A, are also made in 0.05M sodium carbonate pH 9.6 and bound to separate wells of the microtiter plate. After incubation and washing, the immobilized aliquot A and prekallikrein standards are incubated with labelled or enzyme-conjugated monoclonal antibody of the present invention. The amount of the antigen bound by the antibody is then determined by standard assays.

It will be appreciated that the antigen bound by the monoclonal antibody from the untreated aliquot A is a measure of the total antigen: prekallikrein+kallikrein+kallikrein-Cl-inhibitor complex+kallikrein-alpha$_2$-macroglobulin complex+kallikrein-antithrombin III complex. Subtraction of the amounts of kallikrein and kallikrein-inhibitor complexes determined in aliquots B through E, from the total antigen as determined from A, yields a determination of the amount of prekallikrein in the sample.

The monoclonal antibodies of the invention may also be conveniently used to measure the level of human plasma prekallikrein alone by converting any kallikrein present in the specimen to kallikrein-inhibitor complex, and absorbing the complexes from the specimen. The only species remaining in the specimen, capable of binding with the monoclonal antibody, is prekallikrein.

Accordingly, the specimen is incubated with an excess of at least one of the three kallikrein inhibitors, i.e., Cl-inhibitor, alpha$_2$-macroglobulin and/or antithrombin III. By "excess" is meant sufficient kallikrein inhibitor to convert all kallikrein in the specimen to kallikrein-inhibitor complex. The resulting complex, and the kallikrein inhibitor complexes already present in the specimen, are then absorbed from the specimen. Absorbtion is most advantageously achieved by contacting the specimen with a mixture of anti-kallikrein-inhibitor antibodies: (anti-human-Cl-inhibitor antibody, anti-human-alpha$_2$-macroglobulin antibody, and anti-human-antithrombin III antibody) bound to a solid matrix. The antikallikrein inhibitor antibodies may comprise either monoclonal or polyclonal antibodies.

The specimen is then incubated with the immobilized anti-kallikrein inhibitor antibodies to remove the various kallikrein-inhibitor complexes. Next, the specimen is contacted with a monoclonal antibody according to the invention, which antibody binds to an antigenic determinant of prekallikrein. The amount of material bound by the monoclonal antibody, that is, the amount of prekallikrein, is measured by any of the various standard assay means described elsewhere herein.

The instant monoclonal antibodies are thus useful in measuring prekallikrein, kallikrein, kallikrein-Cl-inhibitor complex, kallikrein-alpha$_2$-macroglobulin complex and/or kallikrein-antithrombin III complex levels in the plasma in pathogenic states related to the contact activation of the coagulation pathway. These pathogenic states include, but are not limited to, acquired disorders such as gram negative or positive sepsis, carcinoid syndrome, postgastrectomy syndrome, nephrotic syndrome, type IIa hyperlipoproteinemia, allograft rejection, allergic reactions, typhoid fever, viremia, acute pancreatitis and Rocky Mountain Spotted Fever. The monoclonal antibodies of the invention are also useful in measuring abnormal prekallikrein, kallikrein and kallikrein inhibitor complex levels connected with hereditary disorders such as hereditary angioedema.

The monoclonal antibodies of the present invention are useful in removing prekallikrein and kallikrein from the blood, thereby providing a method of therapy for disease conditions wherein the patient suffers from increased levels of these contact activation proteins. Following removal of excessive amounts of kallikrein and prekallikrein, the blood may be returned to the body. Moreover, since the instant monoclonal antibodies have been demonstrated to inhibit the activity of prekallikrein and kallikrein in the contact activation of the coagulation pathway, these antibodies or their Fab fragments may be used to reduce the level of functional kallikrein in vivo by infusion into the blood stream.

The monoclonal antibodies of the present invention may be easily covalently bound to an immobilized matrix such as CNBr-activated Sephrose, as disclosed in *Methods In Enzymology* 104:3 (1984). Prekallikrein may be purified by passing plasma through such a column containing immobilized monoclonal antibody, and then eluting the bound prekallikrein. Purification of prekallikrein in this manner may take place with or without prior partial purification, such as by ion exchange chromatography.

A column of the type described above may also be used to separate the light and heavy chains of kallikrein since at least three of the antibodies of the present invention are specific for epitopes of kallikrein heavy chain. Moreover, because prekallikrein binds high molecular weight kininogen, and because these plasma proteins do not compete. for binding of the present monoclonal antibodies, columns of this type charged with prekallikrein may be used to purify high molecular weight kininogen. Finally, since at least three of the present antibodies recognize kallikrein even after complexing with Cl-inhibitor, and at least one recognizes kallikrein even after complexing with alpha$_2$-macroglobulin and kallikrein-antithrombin III, they may be used to separate kallikrein-Cl-inhibitor, kallikrein-alpha$_2$-macroglobulin and kallikrein-antithrombin III complexes from other components.

The preparation of the hybridomas of the present invention and the production, purification and characterization of the resulting monoclonal antibodies may be carried out as above. Although the subject monoclonal antibodies were prepared by intraperitoneal injection of hybridomas into mice and harvesting of blood or ascites, antibody may also be obtained by culturing the hybridomas by in vitro techniques known to those skilled in the art.

The four reported hybridomas, namely 6A6, 13H11, 13G11, and 10B6 belong to sub-class IgG$_1$, which means they have the same "constant" region. An antibody to a specific antigen has a "variable" region, which functionally recognizes the antigen, and a constant region. The variable region recognizes antigen regardless of the type of constant region. Thus, monoclonal antibodies exhibiting the characteristics described herein may be of sub-class IgG$_1$, IgG$_{2a}$, IgG$_{2b}$, IgG$_3$, IgM, IgA or other Ig classes. Since the difference in immunoglobulin class (Ig) will not affect the pattern of reactivity of the antibody toward the antigen, it is contemplated that monoclonal antibodies to human plasma prekallikrein are included within the subject invention regardless of Ig class of sub-class.

The method of the present invention for preparing monoclonal antibodies to human plasma prekallikrein, which include immunization, fusion and selection of hybridomas, may be followed to generate cell lines other than the four cell lines disclosed herein. Because individual hybridomas may be identified only by the antibody which they produce, it is contemplated that any hybridoma producing antibody to human plasma prekallikrein is included within the scope of the present invention, as are methods for making such antibodies employing hybridomas. It is further contemplated that splenocytes and myelomas from other vertebrates, such as human, rat, bovine, porcine, etc., not just those of murine origin, may be used to form hybridomas using the methods described herein.

The monoclonal antibodies of the present invention are produced by hybridomas. However, it is contemplated that other methods of cell-immortalization may be used to produce monoclonal antibodies against human plasma prekallikrein. These methods are known to those skilled in the art. For example, human antibody-producing lymphocytes may be immortalized by transformation with Epstein-Barr virus. See, e.g., Chiorazzi et al., J. Exp. Med. 56, 930–35 (1982); Steintz, et al., J. Immunol. 132, 877–82 (1984).

The present invention may be embodied in other specific forms without departing from the spirit or essential attributes thereof and, accordingly, reference should be made to the appended claims, rather than to the foregoing specification, as indicating the scope of the invention.

We claim:

1. A monoclonal antibody produced by a hybridoma formed by fusion of cells from a myeloma line and spleen cells from a non-human vertebrate donor previously immunized with human plasma prekallikrein, which antibody specifically binds to an antigenic determinant of human plasma prekallikrein, which antigenic determinant is also present in kallikrein, and kallikrein-Cl-inhibitor complex, said monoclonal antibody having the ability to inhibit the procoagulant activity of prekallikrein.

2. A monoclonal antibody according to claim 1 produced by a hybridoma formed by fusion of cells from a non-human myeloma line and spleen cells from a non-human donor previously immunized with human plasma prekallikrein.

3. A monoclonal antibody according to claim 1 which binds to an antigenic determinant of prekallikrein, which determinant is also present in kallikrein, kallikrein-Cl-inhibitor complex and kallikrein-alpha$_2$-macroglobulin complex.

4. A monoclonal antibody according to claim 1 which binds to an antigenic determinant of prekallikrein, which determinant is also present in kallikrein, kallikrein-Cl-inhibitor complex, kallikrein-alpha$_2$-macroglobulin complex and kallikrein-antithrombin III complex.

5. A monoclonal antibody according to claim 1 which binds to an antigenic determinant of prekallikrein which is also present on the heavy chain of kallikrein.

6. A monoclonal antibody according to claim 1 which is of the IgG$_1$ sub-class.

7. A monoclonal antibody according to claim 2 wherein the myeloma line and spleen cells are murine.

8. A monoclonal according to claim 7 wherein the hybridoma is formed by fusion of SP2/O-Agl4 myeloma cells and spleen cells from a BALB/c AnSkh mouse previously immunized with purified human plasma prekallikrein.

9. A monoclonal antibody according to claim 1 which inhibits the enzyme activity of kallikrein.

10. A monoclonal antibody according to claim 9 which binds to an antigenic determinant of prekallikrein which is also present on plasma kallikrein but not tissue kallikrein.

11. A monoclonal antibody produced by a hybridoma formed by fusion of cells from a myeloma line and spleen cells from a non-human vertebrate donor previously immunized with human plasma prekallikrein, which antibody specifically binds to an antigen determinant of prekallikrein, which determinant is also present in kallikrein and kallikrein-alpha$_2$-macroglobulin complex.

12. A monoclonal antibody according to claim 11 produced by a hybridoma formed by fusion of cells from a non-human myeloma line and spleen cells from a non-human donor previously immunized with plasma prekallikrein.

13. A monoclonal antibody according to claim 12 wherein the myeloma line and spleen cells are murine.

14. A monoclonal antibody according to claim 12 wherein the hybridoma is formed by fusion of SP2/O-Agl4 myeloma cells and spleen cells from a BALB/c AnSkh mouse.

15. Monoclonal antibody according to claim 2 wherein said hybridoma is the hybridoma deposited as ATCC #HB-8863 or as ATCC #HB-8864.

16. Monoclonal antibody according to claim 4 wherein said hybridoma is the hybridoma deposited as ATCC #HB-8862.

17. Monoclonal antibody according to claim 2 wherein said hybridoma is the hybridoma deposited as ATCC #HB-8865.

18. A monoclonal antibody according to claim 1, which binds to an antigenic determinant of human plasma prekallikrein recognized by monoclonal antibody from hybridoma #HB-8862.

19. A monoclonal antibody according to claim 1, which binds to an antigenic determinant of human plasma prekallikrein recognized by monoclonal antibody from hybridoma #HB-8864.

20. A monoclonal antibody according to claim 1, which binds to an antigenic determinant of human plasma prekallikrein recognized by monoclonal antibody from hybridoma #HB-8863.

21. A composition comprising a continuous cell line producing monoclonal antibody according to claim 1, and a culture medium for said cell line.

22. A composition comprising a continuous cell line producing monoclonal antibody according to claim 2, and a culture medium for said cell line.

23. A composition comprising a continuous cell line producing monoclonal antibody according to claim 1, and a culture medium for said cell line.

24. A cell line selected from the group of cell lines numbered consecutively from ATCC #HB-8862 through ATCC #HB-8865.

* * * * *